United States Patent [19]

Cragoe, Jr. et al.

[11] 4,432,992

[45] Feb. 21, 1984

[54] 4-[5(AND 4)-SUBSTITUTED-2-THIENYL]-3-HYDROXY-3-PYRROLINE-2,5-DIONE INHIBITORS OF GLYCOLIC ACID OXIDASE

[75] Inventors: Edward J. Cragoe, Jr., Lansdale; Clarence S. Rooney, Worcester, both of Pa.; Haydn W. R. Williams, Dollard des Ormeaux, Canada

[73] Assignee: Merck & Co., Inc., Rahway, N.J.

[21] Appl. No.: 91,448

[22] Filed: Nov. 5, 1979

[51] Int. Cl.$^3$ .................. A61K 431/38; C07D 409/04
[52] U.S. Cl. ...................................... 424/274; 548/517
[58] Field of Search .............. 260/326.5 SM; 424/274; 548/517

[56] References Cited

U.S. PATENT DOCUMENTS 3,340,263  9/1967  Stachelln et al. .................... 544/372

OTHER PUBLICATIONS

Liao et al., Arch. Biochem. Biophys., 154, (1973) pp. 68–75.
Haulay J. Pharm. Chim, 24, 1936, pp. 537-548.
G. S. Skinner et al., J. Am. Chem. Soc., 73, (1951) pp. 2230-2233; 70 (1948) pp. 4011-4013.
Randall et al., J. Med. Chem., 22, (1979) pp. 608-614.

Primary Examiner—Paul M. Coughlan, Jr.
Assistant Examiner—D. B. Sringer
Attorney, Agent, or Firm—Raymond M. Speer; Michael C. Sudol, Jr.

[57] ABSTRACT

Novel 4-[5(and 4)-substituted-2-thienyl]-3-hydroxy-3-pyrroline-2,5-diones are disclosed which inhibit glycolic acid oxidase and thus are useful in the treatment and prevention of calcium oxalate kidney stone formation. A novel process for their preparation is also disclosed.

9 Claims, No Drawings

4-[5(AND 4)-SUBSTITUTED-2-THIENYL]-3-HYDROXY-3-PYRROLINE-2,5-DIONE INHIBITORS OF GLYCOLIC ACID OXIDASE

BACKGROUND OF THE INVENTION

Close to 70% of kidney stones in man are composed partially or predominantly of calcium oxalate. There is no satisfactory drug therapy specific for the treatment of calcium oxalate renal lithiasis, nor for prophylactic use by patients prone to recurrent attacks of this disease.

The most common treatment for renal lithiasis due to calcium oxalate consists of surgical removal of stones, control of the diet to restrict calcium or oxalate, and ingestion of large quantities of water to dilute the urine. Attempts at chemotherapy have included the administration of magnesium oxide, calcium carbimide, orthophosphate, cellulose phosphate, isocarboxazide, thiazide diuretics, allopurinol and succinimide. Limited success has been realized by these drug approaches. No drug which specifically inhibits the biosynthetic formation of oxalic acid has previously been developed for the treatment of calcium oxalate renal lithiasis.

The immediate metabolic precursor of the majority of the oxalate in the urine of a typical patient is glyoxylic acid. In turn its most important precursor is glycolic acid. The enzyme glycolate oxidase is able to carry out the oxidation of glycolic acid, through glyoxylic acid, to oxalic acid. Inhibition of this enzyme will, therefore, reduce the concentration of oxalic acid in the kidney and bladder, decreasing the probability that calcium oxalate crystallization will occur. Thus inhibitors of glycolate oxidase provide a specific approach to the prevention and treatment of calcium oxalate renal lithiasis.

Liao, et al, *Arch. Biochem. Biophys.*, 154, 68–75 (1973) have shown that phenyllactic acid and n-heptanoic acid, which are inhibitors of glycolate oxidase, inhibit oxalate biosynthesis in isolated perfused rat liver. These compounds are not sufficiently potent to be useful as drugs.

The preparation of 3-hydroxy-4-phenyl-3-pyrroline-2,5-dione

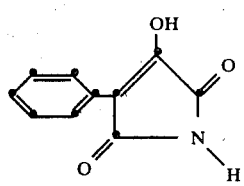

has been described by Harlay, *J. Pharm. Chim.*, 24, 537–48 (1936). 3-Hydroxy-4-aryl-3-pyrroline-2,5-diones are described in U.S. Pat. No. 3,349,263 as intermediates in the preparation of antiphlogistic substances.

A number of 3-hydroxy-4-substitutedphenyl-3-pyrroline-2,5-diones are reported by G. S. Skinner, et al., *J. Am. Chem. Soc.*, 73, 2230 (1951). (In this paper these compounds are referred to as pyrrolidine-2,3,5-trione derivatives). 3-Hydroxy-4-(4-bromo-1-naphthyl)-3-pyrroline-2,5-dione is described by G. S. Skinner, et al., *J. Am. Chem. Soc.*, 70, 4011 (1948).

SUMMARY OF THE INVENTION

It has now been found that novel compounds of the formula:

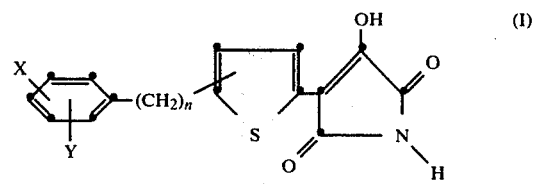

wherein
n is 0 to 2;
X and Y are independently hydrogen, halogen, loweralkyl containing 1 to 4 carbons or a pharmaceutically acceptable salt thereof are potent inhibitors of glycolate oxidase. They are, therefore, useful in the treatment and prevention of calcium oxalate kidney and bladder stone formation.

DETAILED DESCRIPTION

About 70% of all renal calculi contain oxalate as the main component of the matrix. In the majority of patients the condition is associated with a higher than average level of metabolically produced oxalate. The major pathway for biosynthesis of oxalate can be represented as follows:

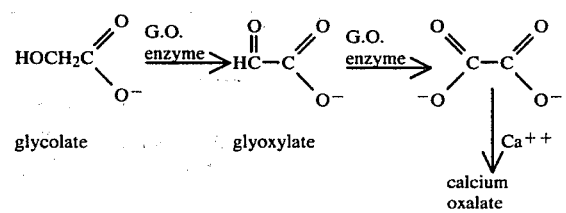

Glyoxylate is the major immediate forerunner of oxalate. An inhibitor of glycolate oxidase (G.O.) will inhibit both the conversion of glyoxylate to oxalate as well as the production of glyoxylate from glycolate. By reducing oxalic acid levels in the urine with the compounds of this invention, the formation of oxalate calculi will be reduced or prevented.

Compounds of formula (I) are potent inhibitors of glycolate oxidase and thus are useful in restricting oxalate levels in the kidney and urine. Further, they are useful in the treatment and prevention of renal disease due to calcium oxalate stone formation in the kidney and bladder. They also may be useful in the treatment of the genetically inherited diseases termed Hyperoxaluria types I and II in which very high levels of metabolic oxalate are present.

Compounds of formula (I) have been unexpectedly found to block the contractions of guinea pigg ileum induced by Slow Reacting Substance of Anaphylaxis (SRS-A). They are ineffective against contractions caused by histamine, which demonstrates specificity against SRS-A. SRS-A is considered a major mediator in human allergic asthma. Thus the compounds of formula (I) are useful in the treatment of allergy, especially allergic asthma.

Compounds of formula (I) can be prepared according to the following general route:

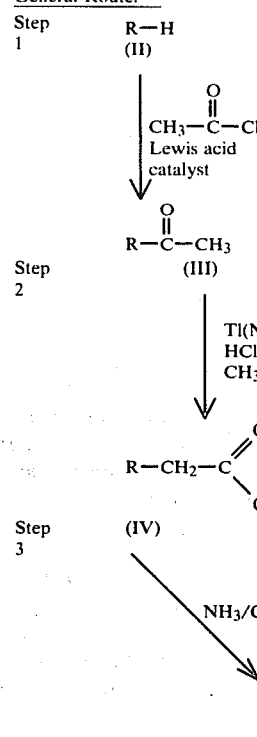

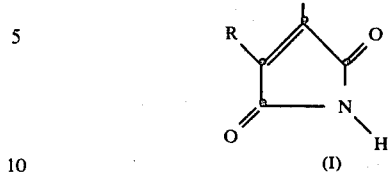

(I)

wherein
R represents substituents at the 4-position of the 3-hydroxy-3-pyrroline-2,5-dione in formula (I) above.

The following examples, given by way of illustration and not to be construed as limiting, further clarify the invention.

GENERAL PROCEDURE FOR THE PREPARATION OF SUBSTITUTED THIENYL ACETOPHENONES

Step 1

The methyl ketones (III) are prepared by acetylation of the parent compound (II) with acetyl chloride and a Lewis acid catalyst under conventional Friedel Craft conditions.

An example of a methyl ketone (III) prepared by this process is set forth in Table I below:

TABLE I

| Compound (III) | Catalyst Solvent | Yield % | MP °C. Solvent | Formula | Analysis Req. | Fd. |
|---|---|---|---|---|---|---|
| [structure: Cl-phenyl-thiophene-C(O)-CH₃] 2-acetyl-5-(4-chlorophenyl)-thiophene | TiCl₄ C₆H₆ | 83 | 119–120 CCl₄ | C₁₂H₉ClOS | C 60.89 H 3.83 S 13.54 | 60.49 4.37 13.53 |

GENERAL PROCEDURE FOR THE PREPARATION OF METHYL SUBSTITUTED THIENYLACETATES (IV)

Step 2

Substituted thienylactic acid esters (IV), are made by the oxidative rearrangement of the corresponding methyl-ketones (III) by the method of E. C. Taylor and A. McKillop, *J. Amer. Chem. Soc.*, 93, 4919 (1971), ibid 95, 3340 (1973). An example of a substituted thienylacetic acid ester (IV) prepared by this process is set forth in Table II below:

TABLE II

| Compound (IV) | Yield % | MP °C. Solvent | Formula | Analysis Req. | Fd. |
|---|---|---|---|---|---|
| [structure: Cl-phenyl-thiophene-CH₂-C(O)-OCH₃] methyl 5-(4-chlorophenyl)-2-thienylacetate | 85 | 84–85 CH₃OH | C₁₃H₁₁ClO₂S | C 58.54 H 4.16 S 12.02 | 58.30 4.33 12.17 |

GENERAL PROCEDURE FOR PREPARING THE SUBSTITUTED ACETAMIDES (V)

An example of a 4-[5-(substituted-2-thienyl)]-3-hydroxy-3-pyrroline-2,5-dione prepared by this process is set forth in Table IV below:

TABLE IV

| Compound (I) | Yield % | MP °C. Solvent | Formula | Analysis Req. | Fd. |
|---|---|---|---|---|---|
| 3-[5-(4-chlorophenyl)-2-thienyl]-4-hydroxy-3-pyrroline-2,5-dione | 51 | 266 dec | $C_{14}H_8ClNO_3S$ | C 55.00<br>H 2.64<br>N 4.58 | 54.79<br>2.44<br>4.34 |

*The compounds of this invention may also be referred to as 3-substituted-4-hydroxy-3-pyrroline-2,5-dione derivatives.

Step 3

The substituted acetic acid esters (IV) are converted to the corresponding amides (V) by treatment with 7½ parts by weight of a saturated solution of ammonia in methanol at room temperature. The progress of conversion to the amide is followed by thin layer chromatography. An example of substituted acetamide (V) prepared by this process is set forth in Table III below:

TABLE III

| Compound (V) | Yield % | MP °C. Solvent | Formula | Analysis Req. | Fd. |
|---|---|---|---|---|---|
| 5-(4-chlorophenyl)-2-thienylacetamide | 95 | 208.5–209 MeCN | $C_{12}H_{11}ClNOS$ | C 57.26<br>H 4.00<br>N 5.56<br>S 12.74 | 56.22<br>4.09<br>5.14<br>12.57 |

GENERAL METHOD FOR THE PREPARATION OF 4-[5(or4)-(Substituted-2-thienyl)]-3-hydroxy-3-pyrroline-2,5-diones

Step 4

A mixture of the substituted acetamide (10 mmole), diethyl oxalate (1.533 g, 10.5 mmole) and dry dimethylformamide (20 ml) is stirred under nitrogen or argon and cooled in an ice-bath. Potassium t-butoxide (2.464 g, 22 mmole) is added in two equal portions 15 minutes apart and the reaction mixture is stirred for about 30 minutes in the ice-bath and then at room temperature overnight. The reaction mixture is poured into ice-water (100 ml). If the potassium salt of the product dissolves, the aqueous mixture is extracted with ethyl acetate (2×35 ml) and then acidified with 6 N hydrochloric acid in order to precipitate the product. The product is either collected by filtration or by extraction with ethyl acetate.

If the potassium salt is not soluble when the reaction mixture is quenched in ice-water, then it is necessary to acidify the resulting suspension and collect the product by filtration. The crude product is generally less pure when obtained in this way.

Compounds may be solvated after recrystallization (with either DMF, dioxane, isopropanol or acetonitrile) and require drying at 110° C./0.05 Torr in order to remove the solvate.

When the above sequence of reactions is performed starting with 2-benzylthiophene there is obtained 3-(5-benzyl-2-thienyl)-4-hydroxy-3-pyrroline-2,5-dione. When the above sequence of reactions is carried out starting with 2-(3,4-dichlorophenyl)thiophene there is obtained 3-[5-(3,4-dichlorophenyl)-2-thienyl]-4-hydroxy-3-pyrroline-2,5-dione. When 3-(4-chlorophenyl)thiophene is utilized as starting material, there is obtained 4-[4-(4-chlorophenyl)-2-thienyl]-3-hydroxy-3-pyrroline-2,5-dione. When 2-(4-methylphenyl)-thiophene is the starting material, there is obtained 4-[5-(4-methyphenyl)-2-thienyl]-3-hydroxy-3-pyrroline-2,5-dione. When 2-(o-chlorobenzyl)thiophene is used as starting material there is obtained 4-[5-(o-chlorobenzyl)-2-thienyl]-3-hydroxy-3-pyrroline-2,5-dione. When 3-phenylthiophene is used as starting material in the above sequence of reactions there is obtained 4-(4-phenyl-2-thienyl)-3-hydroxy-3-pyrroline-2,5-dione.

Included within the scope of the invention are the pharmaceutically acceptable salts of formula (I) compounds. The compounds of formula (I) are strong organic acids with a pKa in the range 2–4. These salts are readily formed with the usual inorganic cations such as sodium, potassium and ammonium. Salts with organic amines such as trimethylamine, triethylamine, n-butylamine and the like are also very stable. The neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt.

The compounds of formula (I) are utilized for the stated utilities for formulating them in a composition such as tablet, capsule or elixir for oral administration. Sterile solutions or suspensions can be used for parenteral administration. About 10 to 200 mg of a compound of formula (I) or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose will be in the 30 to 2000 mg range with the preferred dosage range being 50 to 1000 mg.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coating or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharamceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

What is claimed is:

1. The compounds of the formula:

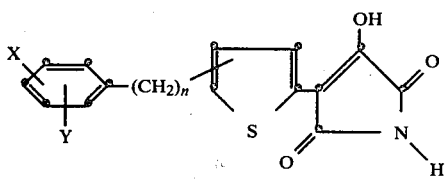

wherein n is 0 to 2;

X and Y are independently hydrogen, halogen, lower alkyl containing 1 to 4 carbons, or a pharmaceutically acceptable salt thereof.

2. The compounds of claim 1 of the formula:

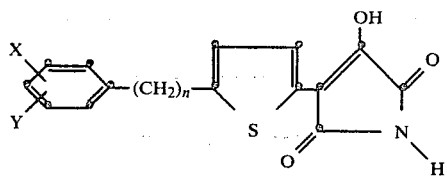

wherein n is 0 to 2;

X and Y are independently hydrogen, halogen, lower alkyl containing 1 to 4 carbons, or a pharmaceutically acceptable salt thereof.

3. The compounds of claim 1 of the formula:

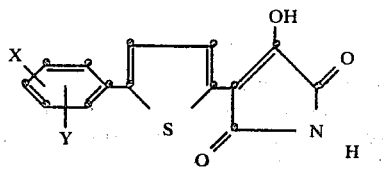

wherein

X and Y are independently hydrogen, halogen, lower alkyl containing 1 to 4 carbons, or a pharmaceutically acceptable salt.

4. The compounds of claim 3 wherein

X and Y are halogen.

5. A compound of claim 3 designated: 4-[5-(4-chlorophenyl)-2-thienyl]-3-hydroxy-3-pyrroline-2,5-dione.

6. A pharmaceutical composition useful in the treatment and prevention of calcium oxalate kidney and bladder stone formation comprising an effective amount of a compound of claim 1 or the pharmaceutically acceptable salts thereof and a pharmaceutically acceptable carrier thereof.

7. A pharmaceutical composition useful in the treatment and prevention of calcium oxalate kidney and bladder stone formation comprising an effective amount of 4-[5-(4-chlorophenyl)-2-thienyl]-3-hydroxy-3-pyrroline-2,5-dione, or the pharmaceutically acceptable salts thereof and a pharmaceutically effective carrier thereof.

8. A method of treating persons afflicted with calcium oxalate kidney or bladder stones or preventing the formation of calcium oxalate kidney or bladder stones which comprises administering to such a patient an effective amount of a compound of claim 1.

9. A method of treating persons afflicted with calcium oxalate kidney or bladder stones, or preventing the formation of kidney or bladder stones, which comprises administering to such a patient an effective amount of 4-[5-(4-chlorophenyl)-2-thienyl]-3-hydroxy-3-pyrroline-2,5-dione.

* * * * *